United States Patent [19]
Dickerson

[11] Patent Number: 5,397,480
[45] Date of Patent: Mar. 14, 1995

[54] PURIFICATION OF AQUEOUS STREAMS

[76] Inventor: J. Rodney Dickerson, 105 Young Dr., Lafayette, La. 70506

[21] Appl. No.: 166,645

[22] Filed: Dec. 13, 1993

Related U.S. Application Data

[63] Continuation-in-part of Ser. No. 856,100, Mar. 23, 1992, abandoned.

[51] Int. Cl.$^6$ .............................................. C02F 1/78
[52] U.S. Cl. ................................. 210/752; 210/760; 210/192; 210/928; 261/DIG. 42; 261/116
[58] Field of Search .............. 210/752, 760, 192, 928; 261/116, DIG. 42

[56] References Cited

U.S. PATENT DOCUMENTS

| | | | |
|---|---|---|---|
| 804,589 | 11/1905 | Enrico | 261/116 |
| 2,447,123 | 8/1948 | Jones | 261/116 |
| 3,445,001 | 5/1969 | LaRaus | 210/760 |
| 3,737,374 | 6/1973 | Stern et al. | 210/928 |
| 3,761,065 | 9/1973 | Rich et al. | 261/116 |
| 4,104,166 | 8/1978 | LaRaus | 210/259 |
| 4,382,044 | 3/1983 | Baumgartner et al. | 261/DIG. 42 |
| 4,696,739 | 9/1987 | Pedneault | 210/192 |
| 4,898,679 | 2/1990 | Siegel et al. | 210/752 |
| 5,004,537 | 4/1991 | Brown | 210/192 |
| 5,053,140 | 10/1991 | Hurst | 210/704 |
| 5,116,574 | 5/1992 | Pearson | 210/760 |
| 5,173,257 | 12/1992 | Pearson | 422/3 |
| 5,273,664 | 12/1993 | Schulz | 210/759 |

Primary Examiner—Cynthia L. Nessler
Attorney, Agent, or Firm—William David Kiesel; Robert C. Tucker

[57] ABSTRACT

Aqueous streams are purified by use of ozone in one or more purification zones wherein the ozone is drawn from one purification zone to another by use of one or more eductors in each purification zone.

9 Claims, 2 Drawing Sheets

PURIFICATION OF AQUEOUS STREAMS

CROSS-REFERENCE TO RELATED APPLICATIONS

This is a continuation-in-part of copending application Ser. No. 856,100, filed Mar. 23, 1992, now abandoned.

FIELD OF THE INVENTION

The present invention relates to a process for purifying aqueous streams which comprises treating the stream in two or more purification zones with an effective amount of ozone. An eductor means is used to both introduce the ozone into each purification zone and to pass any remaining ozone from one purification zone to another.

BACKGROUND OF THE INVENTION

A substantial number of aqueous streams must be treated to meet governmental laws and regulations to certify them for drinking purposes or for release into the environment. Non-limiting examples of such aqueous streams include: those emanating from municipal water supplies; those waste water streams resulting from various chemical, petrochemical, and refining processes; and, those resulting from various other industries such as the pulp and paper industry. Contaminated ground water streams must also be treated depending on their intended use. Such aqueous streams typically contain one or more impurity, such as suspended matter, dissolved organic constituents, dissolved mineral matter, and microorganisms. The pulp and paper industry is faced with an additional problem of having to reduce color from its waste water streams. The color, which usually develops when wood is pulped, is derived primarily from the non-carbohydrate constituents of the wood, such as lignin. Lignin and certain extraneous components contain sites that can, under certain conditions, be readily converted to colored (chromophoric) groups. These constituents are generally chlorinated organic compounds which vary in molecular weight. The chlorinated lignins are typically high molecular weight molecules that tend to be stable against biodegradation. Therefore, it is desirable to break these high molecular species into smaller components which will be more susceptible to biodegradation.

Various methods have been developed over the years for purifying aqueous streams, including methods for removing or destroying color components. Early methods of treatment involved the use of aeration with a gas having a relatively high oxygen content, over a period of several days, to biodegrade various bacterial and organic substances. This typically resulted in the waste stream being environmentally safe except for the presence of color components which are not easily destroyed by aeration. Before the introduction of strict environmental laws and regulations, such streams, after aeration, could merely be fed into a moving river or stream, where their color would be diluted. The drought and resultant low flow conditions of receiving streams in the United States in the 1980's has caused increased concern about the environmental impact such colored waste streams have when released into rivers, streams, etc. Consequently, there is a substantial need to further purify these streams to a greater degree, at reasonable cost, so they will have little, if any, negative impact when released into the environment.

Other conventional methods for purifying aqueous streams include the addition of lime, activated carbon, or both, to precipitate, and adsorb colored bodies. In the case of lime, the resulting precipitate is typically gelatinous in nature, low in solids, difficult to separate, and is extremely resistant to dewatering by accepted methods. This presents a disposal problem of its own. Furthermore, much of the lime is lost during the process, adding greatly to the economics of the process itself. Activated carbon, which removes color components by adsorption, has also been used, but has proved to be uneconomical. That is, like the use of lime, the use of activated carbon results in the disadvantages of high cost and the continuous need for solids disposal or regeneration of reactant.

Still other conventional methods for treating waste water streams include the use of oxidizing agents, including oxygen, ozone, air, peroxides, permanganates, chromates, metal oxides, mineral acids, and organic oxidizing agents, such as peracetic acid. Further, U.S. Pat. No. 3,737,374 teaches the use of ozone to reduce the molecular weight of the lignins to less than about 10,000, thereby reducing its color intensity. These lower molecular weight species are also more susceptible to biodegradation because they are more easily digested by microorganisms. In fact, ozone is becoming the oxidizer of choice for purifying these streams.

While the above methods have met with various degrees of success in clarifying waste water streams which contain color bodies, there still remains a need in the art for ever more efficient processes for clarifying such streams.

SUMMARY OF THE INVENTION

In accordance with the present invention, there is provided a process for purifying an aqueous waste stream in a purification process unit comprised of two or more serially connected purification zones, inclusive of a lead purification zone and a tail purification zone, wherein each purification zone contains a top section and a bottom section, and wherein each purification zone contains at least one eductor means which are driven by recycle liquid to draw ozone into the bottom section of said purification zone; the process which comprises:

(a) flowing said aqueous waste stream to be purified serially through the purification zones, starting with the lead purification zone, wherein said stream is introduced at the top section of the lead purification zone, flows to the bottom section, where it exits and is passed to the top of the next downstream purification zone, until the tail purification zone, where it exits the process unit;

(b) treating the aqueous stream in each of the purification zones with a counter-current flow of an effective amount of ozone, which ozone is drawn into each of the purification zones by the one or more eductor means, which eductor means are comprised of a first and second substantially uniform diameter tubular member each having an inlet end and an outlet end and each being co-axial to each other, said first tubular member being of a smaller diameter than said second tubular wherein its outlet end extends into said second tubular member to a predetermined distance short of the outlet end of said second tubular member, the outlet end of said first tubular member having attached thereto a discharge nozzle, said outlet end of said second tubular member having an axially disposed orifice of substantially smaller diameter than the diameter of said second tubular member, wherein said first tubular member is in fluid communication with said recycle liquid which is forced down said first tubular member and discharged from said nozzle in the form of droplets, thereby causing ozone to be drawn into said second tubular member which is in fluid communication which an ozone source, said ozone being entrained in said droplets and exiting said second tubular member at said orifice.

In preferred embodiments of the present invention, an effective amount of ozone is introduced into the tail purification zone and is moved serially from purification zone to upstream purification zone counter-current to the aqueous stream flowing through the purification zones.

In another preferred embodiment of the present invention, all of the eductor means are driven by recycle liquid from only one of the purification zones.

DETAILED DESCRIPTION OF THE INVENTION

Figure 1:
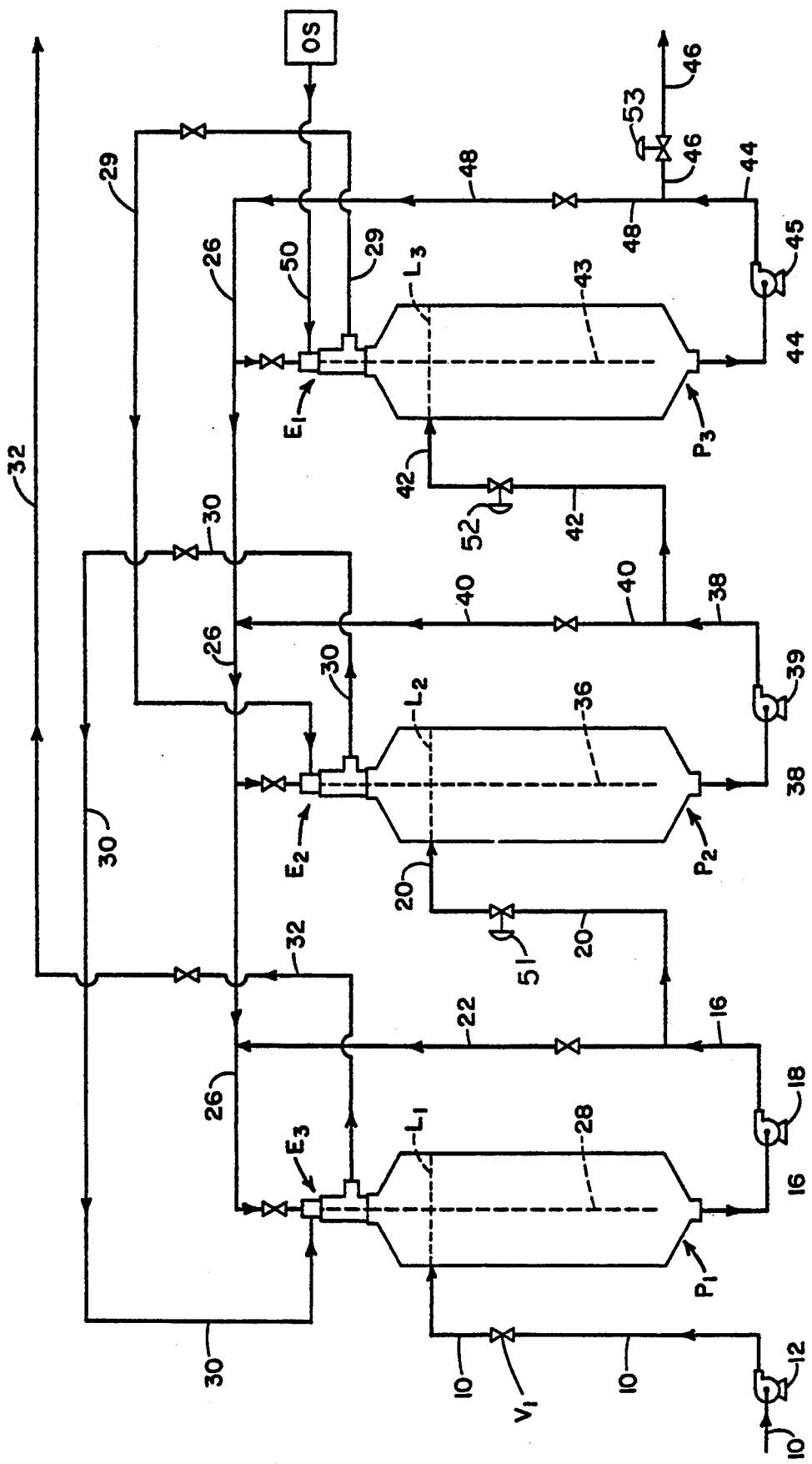
FIG. 1 is simplified schematic flow diagram of one preferred embodiment of the present invention wherein three purification zones, or vessels are used. Each vessel has an eductor means vertically disposed therein and each eductor means is driven by recycle liquid from the vessel in which it is disposed.
Figure 4:
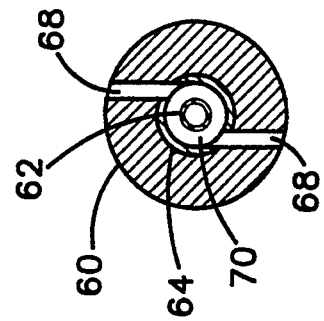
FIG. 4 is a cross-sectional view in a horizontal plane indicated by line 4—4 in FIG. 2. This Figure shows a preferred arrangement of inlets to the educator means for enhanced gas flow.

The instantly claimed invention can be practiced on any aqueous stream which contains an unacceptable level of impurities, such as suspended matter, organics, dissolved mineral matter, dioxins, microorganisms, and color bodies. Non-limiting examples of such aqueous streams include effluent streams from such industries as the chemical industry, the pulp and paper industry, petrochemical and petroleum refining, as well as municipal water supplies and aquifers. Effluent aqueous streams from the pulp and paper industry also contain various color components which need to be removed before the stream can be released into a river, stream, etc. The predominant color component in such effluent streams results from the presence of lignins which are present in wood and which are found in amounts ranging from about 17 to 32 wt. %, on a moisture free basis. After pulping and bleaching with chlorinated compounds, the lignins of the effluent stream are generally relatively high molecular weight chlorinated molecules that tend to be stable against biodegradation.

Strong oxidizing agents, such as ozone, are capable of breaking these high molecular weight molecules into smaller molecules, which are more biodegradable. Ozone is a highly reactive gas at ambient temperatures and pressures and must be generated on site due to its reactive nature by using either compressed air or oxygen as a feed gas. The ozone is introduced with a feed, or carrier gas, preferably air, into each purification zone where at least a portion of it dissolves in the aqueous stream and reacts with impurities of the stream. The amount of ozone used is the practice of the present invention should be an effective amount. That is, at least that amount which will react with the contaminants of the stream. Typically such an amount will be at least about 1 wt. % in the carrier gaseous stream which is preferably air. The carrier gaseous stream may also be oxygen. In practice the amount of ozone in the carrier gas will range from about 1 to 4 wt. % for air as a carrier gas, and from about 2 to 10 wt. % when oxygen is the carrier gas. One method to determine the precise amount of ozone necessary for any given stream and set of process conditions is to introduce enough ozone into the unit until breakthrough occurs. The amount of ozone is then reduced until the point is reached where no breakthrough of ozone is detected. By breakthrough of ozone is meant that so much ozone is used that there is excess left of passing through the purification zones and must be vented to the atmosphere or recycled. The diffusion of ozone into the stream is influenced by various factors, including the ozone concentration in the feed gas, the temperature of the aqueous stream, and process pressures. While most conventional ozone contactors are designed to maximize the mass transfer of ozone from the feed gas to an aqueous medium, they all fall short of the mark. On the other hand, the eductor means used in the present invention are capable of giving improved mass transfer of ozone to the aqueous stream. They are also used to draw any unreacted ozone from one purification zone to another.

Turning now to FIG. 1 hereof, there is shown a preferred three vessel process unit of the present invention wherein an aqueous waste stream to be purified is fed via line 10 into lead purification zone $P_1$ where it is maintained at a level $L_1$. Temperatures employed in any of the purification zones will typically be the inherent temperature of the aqueous stream being treated. While the temperature is not critical for the practice of the present invention, that is, for the ozone to react with impurities in the stream, elevated temperatures are preferred because the rate of reaction will increase with increased temperatures. Pressures in the purification zones will preferably be from about 10 psig to about 100 psig. The aqueous stream can be fed through line 10, through valve $V_1$, by use of a pump 12. The aqueous stream flows from the top of purification zone $P_1$ to the bottom and exits via line 16 where it is pumped via pump 18 to the top of purification zone $P_2$ via line 20. A portion of the treated waste water stream can be recycled via line 22 where it can be used to drive eductor $E_3$ to draw any unreacted ozone from purification zone $P_2$ via line 30. The ozone is originated at ozone source OS, and is passed counter-current through the purification process unit from purification zone $P_3$, to purification zone $P_2$, to purification zone $P_1$, by the respective eductors. Any unreacted ozone is vented via line 32.

Figure 3:
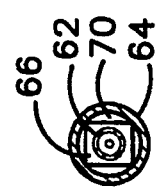
FIG. 3 is a cross-sectional view in a horizontal plane indicated by line 3—3 in FIG. 2.
Figure 2:
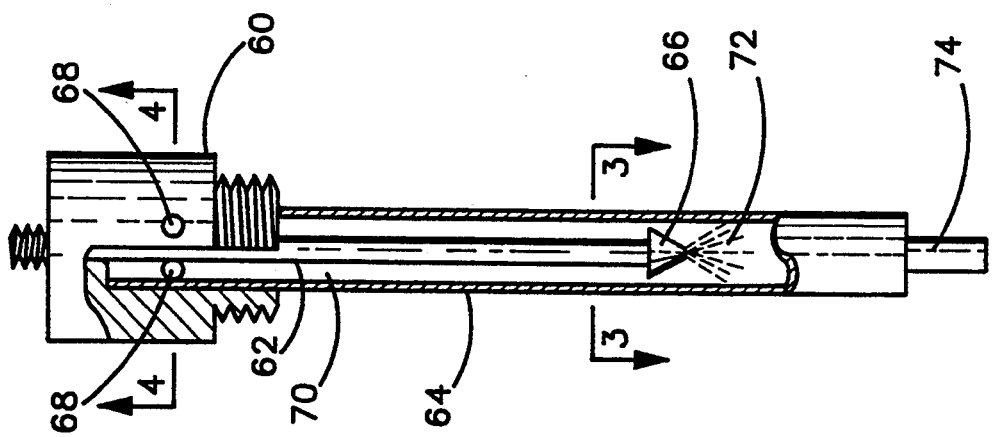
FIG. 2 is a cross-sectional planar view a an eductor which can be used in the practice of the present invention.

The eductor means of the present invention utilizes a high pressure jet of liquid to create a partial vacuum at an intake opening to draw another fluid (ozone in this figure) from a sump or reservoir. FIGS. 2 and 3 hereof depict the eductor means of the present invention. For example, the eductor means is vertically disposed in the purification zone and is sealing attached at bulkhead 60. A smaller diameter driver tubular member 62 is provided within a larger tailpipe member 64. As a liquid, preferably a recycle stream, is driven at relatively high pressures through the driver tubular member 62, a partial vacuum is created at a point above outlet nozzle 66 which is preferably stabilized against excessive vibration by being in contact with the inner wall of tailpipe member 64 at 3 or more points, more preferably at 3 or 4 points. While outlet nozzle 66 is shown in FIG. 2 hereof as being triangular in shape, it is understood that other shapes may also be used as long as they do not interfere with the intended function of the nozzle. Preferred shapes are those having relatively smooth, or rounded, surfaces to enhance the flow of a gas like ozone. This partial vacuum draws ozone through inlet 68 and through the annular space 70 which is formed between the driver tubular member and the internal wall of the tailpipe member. The ozone becomes entrained in the spray of fine droplets 72 where mixing is thorough and reaction of ozone with impurities is virtually instantaneous. The drive stream, with ozone entrained therein, is compressed at the end of the tailpipe member because the diameter of outlet orifice 74 is smaller than the diameter of the tailpipe. This compression assures that a greater amount of the ozone dissolves and becomes entrained as fine bubbles within the droplets of the driver liquid. It is preferred that the length of outlet tubular member 74 be from about 3 to 12 inches, more preferably from about 4 to 8 inches, and most preferably from about 5.5 to 6.5 inches. The preferred distance from the outlet nozzle 66 to the bottom end of tailpipe member 64 is about 5 to 7 inches, preferably about 6 inches. It is also preferred that the inside diameter (I.D.) of outlet tubular member 74 be from about $\frac{1}{4}$ to $\frac{3}{4}$, preferably about $\frac{1}{2}$ the I.D. of tailpipe member 64. Also preferred is that the outside diameter (O.D.) be no more than about $\frac{1}{2}$ the I.D. of tailpipe member 64. It is preferred that the I.D. of drive tubular member 62 be substantially equal to the I.D. of outlet tubular member 74.

As the stream exits the tailpipe member at the bottom of the purification zone, any excess ozone beyond the solubility limits of the ozone in the driver liquid, plus dissolved gas that is released due to pressure drop at the exit of the tailpipe member, forms as "micro-fine" bubbles which will contain any unreacted ozone. The bubbles rise in the purification zone towards the surface where they can contact and react with impurities in the aqueous stream. Any volatile organic components will tend to be stripped into the gas bubbles as the bubbles rise and are released at the surface of the liquid stream in the vessel. The reaction will continue in the gas phase as the ozone reacts with the organic vapors.

The eductors used in the practice of the present invention act as a pump which draws ozone from purification zone to purification zone, while providing a means of intimately contacting the ozone with the aqueous stream being treated. Also, the eductor means allows ozone to be generated at a relatively low pressure, preferably at less than about 20 psia, and pumped to virtually any pressure for reaction.

Returning now to FIG. 1, the recycle waste stream of line 22, which is fed to line 26, is the liquid which is forced under a high pressure through the driver tubular member and tailpipe member represented by the numeral 28 of eductor means $E_3$ to the bottom of the purification zone. As the jet of recycle liquid is passing down the driver tubular member, the partial pressure which it creates draws unreacted ozone from purification zone $P_2$ through line 30. During the passage of ozone and recycle liquid down the driver tubular member, mass transfer of ozone to liquid occurs. Any remaining unreacted ozone is vented via line 32. If the aqueous stream being treated contains a substantial amount of color, the level of color reduction which will occur in this lead purification zone will be about 30% to 90%, more typically about 40% to 80%. The concentration of ozone is balanced against recycle rate since lower concentrations mean a higher recycle rate for a given dosage of ozone. However, as ozone concentration increases, so does capital investment and operating cost to produce the ozone. Thus, it is preferred that the ozone concentration be from about 1 to 3.5 wt. % in the carrier gas. As previously stated, one of the advantages of the present invention is that lower concentrations of ozone can be used more effectively than with conventional processes.

The waste water effluent stream from purification zone $P_1$ is passed via lines 16 and 20 to purification zone $P_2$ where it is maintained at a level $L_2$. As in purification zone $P_1$, the waste stream will flow to the bottom of the zone and come into contact with ozone which has been introduced at the bottom of the zone via the driver tubular member and tailpipe member, denoted by the numeral 36 of eductor means $E_2$, which is driven by recycle waste waster from purification zone $P_2$ via lines 38, 40, and 26. The unreacted ozone from purification zone $P_2$ is the source of ozone for purification zone $P_1$ and is passed to said zone $P_1$ via line 30 by the partial vacuum created by eductor means $E_3$. That is, as the jet of recycle waste water is passed down driver tubular member 28, a situation is achieved wherein the pressure at the top of the inlet of the eductor means is higher than that at the bottom of the eductor means. This pressure differential causes the ozone to be drawn into said eductor means $E_3$ via line 30. Similarly, recycle liquid from purification zone $P_2$ is passed via lines 40 and 26 to drive eductor means $E_2$. This is accomplished by passing the recycle liquid at a high velocity down the driver tubular and tailpipe assembly 36 where any unreacted ozone from purification zone $P_3$ is drawn via line 29 into said eductor means. Any excess unreacted ozone can be vented via line 32. The color reduction which results in this second purification zone $P_2$ will typically be from about 20% to 60%, more typically about 25 to 50%, of the color remaining in the stream after treatment in purification zone $P_1$.

The aqueous stream from purification zone $P_2$ is fed via line 38, pump 39, and line 42 to purification zone $P_3$. This waste stream, as in the other purification zones is maintained at a level $L_3$ and flows downward and exits purification zone $P_3$ where it can be collected or released to the environment via line 44, pump 45 and line 46. A portion of the stream can be recycled via lines 44, 48, and 26 and used to drive eductor means $E_1$, which draws ozone via line 50 from ozone source OS and down the driver tubular member and tailpipe member, denoted by the numeral 43. FIG. 1 also allows for the capability of driving all of the eductor means with recycle liquid from purification zone $P_3$ only via pump 45 and lines 48 and 26. As in the second purification zone, the remaining color in the effluent stream from the second purification zone will be reduced another 20 to 60%. The level of liquid in each purification zone can be controlled by level control valves, such as those identified as 51, 52, and 53 in FIG 1.

The above described process scheme represents one preferred embodiment wherein ozone is introduced at the opposite end of the process unit than the aqueous stream being treated and wherein each is passed through the unit counter-current to the other. The advantage of such a process scheme is that as the aqueous stream passes from purification zone to purification zone, there is left in each succeeding zone the more difficult to oxidize color components. Therefore, by the time the waste stream reaches the tail purification zone, the majority of the color components which are left are the more difficult to oxidize. Consequently, it is this purification zone which needs the highest concentration of ozone. Thus, the preferred mode of practicing the present invention has various advantages over more conventional processes. For one, the purification zone which contains the highest concentration of hardest to oxidize color components will also contain the highest concentration of ozone. For another, a greater mass transfer of ozone to aqueous stream occurs because of the use of at least one eductor means in each purification zone. That is, mass transfer of ozone to liquid occurs in the driver tubular member and tailpipe member of the eductor means. Still another advantage is that any unreacted ozone is drawn to another purification zone by use of the eductor means of the receiving purification zone.

It will be understood that the term "purification zone" may mean an individual reaction vessel or separate zones within one reaction vessel. It is preferred that each purification zone be a separate reaction vessel. While FIG. 1 hereof shows three reaction vessels, each having one eductor means, it is understood that the present invention can be practiced with less or more vessels and with one or more eductors means in each vessels. It is also to be understood that the ozone need not flow counter-current throughout the process unit, but may flow concurrent with the aqueous stream. Further, fresh ozone may be introduced into any one or more of the purification zones. Still further, the eductor means for all of the purification zones may be driven by recycle liquid from only one purification zone, preferably the tail purification zone.

The following examples are presented by illustrative purposes only and should not be taken as limiting the invention in any way.

EXAMPLES—EXPERIMENTAL APPARATUS

A purification process unit comprised of four serially connected 50 gallon vessels was used for the examples to follow. Each vessel contained an eductor vertically disposed therein, similar to the one shown in FIG. 2 hereof, wherein recycle liquid from the fourth vessel was used to drive all of the eductors. The tailpipe member of the eductor extended to the bottom quarter of the vessel. A manifold assembly was provided so that fresh ozone could be simultaneously introduced into any one or more of the vessels. A means was also provided to allow unreacted ozone from any of the vessels to be passed to the next upstream or downstream vessel.

Color analysis for each of the following examples was performed in accordance with EPA Standard Method 2120C by use of a Bausch & Lomb Model 501 spectrophotometer. Samples were diluted to an appropriate level and the pH adjusted to about 7.4 to 7.6. Sulfuric acid can be used for alkaline streams and sodium hydroxide for acidic streams. The diluted samples were filtered to remove turbidity and a filtrate sample was transferred to a 1 cm absorption cell and color values determined from the spectrophotometer at a wave length of 465 nm. The spectrophotometer was standardized at 500 APHA color units (pcu). Any sample reading less than 100 APHA color units was retested at a lower dilution.

Example 1 (D-1).

An aqueous stream having a color intensity of 2214 pcu, was introduced into the lead, or first, vessel. The flow rate of the stream was 7.5 gal/min (gpm) (25 minute retention time). Fresh ozone was drawn into the third vessel by the eductor means of that vessel which was driven by recycle liquid from the fourth vessel. The concentration of ozone in air, the feed gas, was about 3.8 wt. %, which corresponded to about 116 ppm. Any unreacted ozone from the third vessel was drawn into the second vessel by the eductor means of the second vessel which was also driven by recycle liquid from the fourth vessel. Again, any unreacted ozone from this second vessel was drawn into the lead vessel by the eductor means from the first vessel, which again, was also driven by recycle liquid from the fourth vessel. Any unreacted ozone from the lead vessel was vented. The ozone for the fourth, or tail, vessel was the ozone which was entrained in the treated aqueous stream which was passed from the third vessel.

A measurement of the unreacted ozone from the lead vessel indicated an ozone utilization for the entire unit (all four vessels) of about 81%, based on the total amount of ozone introduced into the unit through the third vessel, the only point of introduction. The color intensity of the treated aqueous stream in each of the vessels was measured and the results are shown in Table I below.

Example 2 (D-2)

The procedure of Example 1 was followed except the flow rate of the aqueous stream was 10 gpm (20 minute retention time) and the ozone concentration in air introduced into the third vessel was 4.4 wt. %, or 101 ppm. Ozone utilization was found to be 88%, and the color intensity of the treated aqueous stream in each vessel was measured and the results are presented in Table I below.

TABLE I

| Example | pcu Initial | pcu Vessel 1 | pcu Vessel 2 | pcu Vessel 3 | pcu Vessel 4 |
| --- | --- | --- | --- | --- | --- |
| 1 | 2214 | 1709 | 1509 | 1146 | 1082 |
| 2 | 2435 | 1930 | 1616 | 1353 | 1296 |

The above table evidences the efficient use of ozone in the practice of the present invention.

Example 3 (C-1)

A procedure similar to the procedure of Example 1 was followed except that fresh ozone was introduced into each of the second, third, and fourth vessels. Further, ozone from the fourth vessel was passed counter-current through each vessel, by use of each upstream eductor means, to the flow of the aqueous stream. The concentration of ozone in air was 4.76 wt. %, which corresponded to 197 ppm. The flow rate of the aqueous stream was 5 gpm (40 minute retention time). Again, the color intensity of the aqueous stream in each of the vessels was measured and the results are presented in Table II below. The ozone utilization was found to be 73%.

Example 4 (C-2)

The procedure of Example 3 was followed except the concentration of ozone was 2.3 wt. %, or 95 ppm. The color intensity for treated aqueous stream for each vessel is found in Table II below. Ozone utilization was found to be 82%.

TABLE II

| Example | pcu Initial | pcu Vessel 1 | pcu Vessel 2 | pcu Vessel 3 | pcu Vessel 4 |
|---|---|---|---|---|---|
| 3 | 2257 | 1329 | 768 | 478 | 392 |
| 4 | 2257 | 1361 | 792 | 424 | 328 |

Example 5-8 (Comparative)

This example was performed with equipment and by a procedure which is representative of conventional commercial techniques for removing color from aqueous streams.

The equipment used in this example was a 720 gallon enclosed stainless tank which was divided into 6 substantially equal compartments. The compartments are formed by internal walls which extended from the bottom of the tank and ended at some point before reaching the top of the tank. Thus, fluid can flow from one compartment to the next downstream compartment by flowing over the top of the wall separating the two compartments. The bottom of each compartment contained a diffuser stone in fluid communication with an ozone source, thereby allowing ozone to be diffused at the bottom of each compartment. Each compartment also contained an ultraviolet lamp which could be turned on an off as desired. There was also provided a source of hydrogen peroxide.

Four runs were made with an aqueous stream contaminated with color components. Two runs (Examples 5 and 6) were made at a stream retention time in the tank of about 30 minutes and an ozone level of about 225 ppm, and two others (Examples 7 and 8) at a retention time of about 90 minutes and an ozone level of about 200 ppm. For each of the two sets of runs, one was performed with ozone only and the other with ozone and UV light. The temperature of the stream was about 27° C. to 30° C. with a color intensity of about 2500 pcu. The stream flowed into the bottom of the first compartment, filled that compartment, and flowed over the walls separating each compartment until it exited at the bottom of the last compartment. The color intensity of the stream exiting the sixth compartment was measured as set forth in the above examples. The level of ozone which was diffused into each compartment was from about 1 to 2.5 wt. % in air. The results are shown in Table III below.

TABLE III

| Example | Initial pcu | $O_3$ Level ppm | UV Light | % Color Reduction |
|---|---|---|---|---|
| 5 | 2500 | 225 | OFF | 50 |
| 6 | 2500 | 225 | ON | 50 |
| 7 | 2500 | 200 | OFF | 47 |
| 8 | 2500 | 200 | ON | 35 |

The above table illustrates that the above method, which is conventional in the industry, is not as effective for the reduction of color in color contaminated streams as is the present invention which employs eductors for diffusing ozone into the stream and to draw unreacted ozone from one purification zone to another. This table also shows that the use of ultraviolet light has substantially no effect for reducing the color intensity when compared with the use of ozone alone.

Examples 9-11 (Comparative)

Three separate runs were performed in accordance with the above procedures except the stream was treated with 220 ppm of ozone in each compartment, and the retention time was 90 minutes. One run (Example 9) was done with 220 ppm ozone only; another (Example 10) with 110 ppm ozone with 110 ppm of hydrogen peroxide; and a third (Example 11) with 220 ppm of hydrogen peroxide only. The results on shown in Table IV below.

TABLE IV

| Example | Initial pcu | $O_3$ Level ppm | $H_2O_2$ ppm | % Color Reduction |
|---|---|---|---|---|
| 9 | 2500 | 220 | — | 30 |
| 10 | 2500 | 110 | 110 | 26 |
| 11 | 2500 | — | 220 | 3 |

The above table shows that even when hydrogen peroxide is used along with ozone, color reduction is not as effective as the present invention which uses eductors to diffuse the ozone into the liquid medium being treated.

What is claimed is:

1. A process for purifying a liquid waste stream in a purification process unit comprised of two or more serially connected separated purification zones, inclusive of a lead purification zone and a tail purification zone, wherein each purification zone contains a top section and a bottom section, and wherein each purification zone contains at least one eductor means which is driven by a portion of said liquid waste stream recycled in a manner to draw ozone into said bottom section of said purification zone; the process which comprises:

(a) flowing said liquid waste stream to be purified serially through said purification zones, starting with said lead purification zone, wherein said liquid waste stream is introduced at said top section of the said lead purification zone, flows to said bottom section, where said liquid waste stream exits and is passed to said top section of the next downstream purification zone, and continuing similarly through each of said purification zones until said liquid waste stream passes through said tail purification zone, where said liquid waste stream exits said purification process unit;

(b) treating said liquid stream in each of said purification zones with a counter-current flow of an effective amount of ozone, which ozone is drawn into the bottom section of each of said purification zones by the one or more eductor means positioned in each of said purification zones, wherein each of said eductor means are comprised of a first substantially uniform diameter tubular member and a corresponding second substantially uniform diameter tubular member, each of said first and second corresponding tubular members of one of said eductor means having an inlet end and an outlet end and each of said first and second corresponding tubular members of one of said eductor means being coaxial to each other, each of said first tubular member in one of said eductor means being of a smaller diameter than said corresponding second tubular member of the same eductor means wherein said outlet end of said first tubular member extends into said corresponding second tubular member of the same educator means to a predetermined distance short of said outlet end of said corresponding second tubular member of the same eductor means, said outlet end of each of said first tubular member having attached thereto a discharge nozzle, said outlet end of each of said corresponding second tubular member having an axially disposed orifice of substantially small diameter than the diameter of said corresponding second tubular member, wherein said first tubular member is in fluid communication with the recycled portion of said liquid waste stream which is forced down said first tubular member and discharged from said discharge nozzle in the form of droplets, thereby causing ozone to be drawn into said second tubular member which is in fluid communication with an ozone source, said ozone being entrained in said droplets and exiting said second tubular member at said orifice.

2. The process of claim 1 wherein said eductor means for each purification zone is driven by a portion of said liquid waste stream from said purification zone in which said eductor means is located.

3. The process of claim 1 wherein said eductor means for all of said purification zones are driven by a portion of said liquid waste stream only from said tail purification zone.

4. The process of claim 1 wherein each purification zone represents a separate reaction vessel.

5. The process of claim 1 wherein fresh ozone is fed into said tail purification zone and is passed counter-current to the flow of liquid waste stream by use of each successive upstream eductor means.

6. The process of claim 1 wherein said fresh ozone is simultaneously drawn into two or more of said purification zones.

7. The process of claim 1 wherein four purification zones are present.

8. The process of claim 1 wherein said liquid waste stream being treated is a stream selected from a group consisting of municipal water supplies; those waste water streams resulting from various chemical, petrochemical, and refining processes; and, those resulting from the pulp and paper industry.

9. The process of claim 8 wherein said liquid waste stream is one resulting from said pulp and paper industry.

* * * * *